United States Patent
Hoelzel et al.

(10) Patent No.: US 6,231,843 B1
(45) Date of Patent: *May 15, 2001

(54) HAIR SHAMPOO HAVING GLOSS-ENHANCING PROPERTIES

(75) Inventors: Hans Hoelzel, Fraenkisch-Crumbach; Manuela Hannich, Hochheim; Gisela Schaefer, Reinheim, all of (DE)

(73) Assignee: Wella Aktiengesellschaft, Darmstadt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,058
(22) PCT Filed: Apr. 21, 1998
(86) PCT No.: PCT/EP98/02351
§ 371 Date: Dec. 28, 1998
§ 102(e) Date: Dec. 28, 1998
(87) PCT Pub. No.: WO98/51264
PCT Pub. Date: Nov. 19, 1998

(30) Foreign Application Priority Data

May 15, 1997 (DE) ............................. 197 20 366

(51) Int. Cl.[7] ...................................... A61K 7/06
(52) U.S. Cl. ................. 424/70.19; 424/70.1; 424/70.21; 424/70.22; 424/70.31; 510/119
(58) Field of Search ................... 424/70.1, 70.22, 424/70.21, 70.19, 70.31, 401; 510/119

(56) References Cited

U.S. PATENT DOCUMENTS 5,785,962 * 7/1998 Hinz et al. ........................ 424/70.22

OTHER PUBLICATIONS

Die Kosmetische Praeparate, by Andreas Domsch, 4. Auflage, Band 2, pp. 212–230.

* cited by examiner

*Primary Examiner*—Thurman K. Page
*Assistant Examiner*—Brian K. Seidleck
(74) *Attorney, Agent, or Firm*—Michael J. Striker

(57) ABSTRACT

The hair cleaning preparation for improving the shine of the hair is an aqueous solution or emulsion which contains water; from 5 to 50 percent by weight of an anionic, nonionic and/or amphoteric surfactant compound; from 2 to 10 percent by weight of a mixture of at least two fruit acids selected from the group consisting of lactic acid, citric acid, maleic acid, tartaric acid, gluconic acid, fumaric acid and succinic acid; from 0.2 to 2 percent by weight of at least one ingredient selected from the group consisting of pantothenol, pantothenic acid and esters of pantothenic acid and at least one cosmetic ingredient selected from the group consisting of perfume oils, preservatives and pH buffer substances. This hair cleaning preparation does not contain any oily or greasy ingredients.

6 Claims, No Drawings

HAIR SHAMPOO HAVING GLOSS-ENHANCING PROPERTIES

This application is a 371 of PCT/EP98/02351, filed Apr. 21, 1998.

BACKGROUND OF THE INVENTION

1. Field of the Invention

The subject of the present invention is a clear or pearlescent hair cleaning preparation containing water, with properties for improving the shine.

2. Prior Art

It has long been one of the goals of hair cosmetics to increase the shine of hair, because this enhances the attractiveness of the hairdo and the entire appearance of the person.

The shine of an article is dependent on its surface property. The rougher its surface, the greater the proportion of diffusely reflected light, and thus the less is its shine. With hair as well, the shine depends on its surface property. Hair damage causes a change in the outermost layer of the hair, the cuticle, which is formed of cells arranged like fish scales. These cuticle scales then protrude irregularly away from the hair, causing roughness of the hair surface, by which the incident light is reflected diffusely. To smooth the rough surface, until now cosmetic preparations have been used that also contain mineral oils from various fractions, vaseline, natural lipids such as oils, wax or resins, and recently above all silicone oils. The disadvantage of these substances is in part their poor biodegradability and the resultant greasy look to the hair, and sometimes problems of physical tolerance. This type of shine also lasts only till the next time the hair is washed, when the glossy coating is then removed again.

SUMMARY OF THE INVENTION

The object is therefore to achieve smooth and regeneration of the surface of hair without adding greasy or oily ingredients to hair cosmetics. This object is attained by the hair cleaning preparation of the invention, which differs from conventional shampoos in the addition of a mixture of fruit acids and pantothenol or one of its derivatives.

This object is attained by a hair cleaning preparation with properties for improving the shine, characterized in that it contains from 5 to 50 weight percent, preferably 20 to 25 weight percent, of a surfactant or a surfactant mixture, from 2 to 10 weight percent, preferably 2 to 5 weight percent, of a mixture of fruit acids, and from 0.2 to 2.0 weight percent of pantothenol or one of its derivatives.

The hair cleaning preparation of the invention is preferably in the form of an aqueous solution or emulsion, for instance a gel, cream or shampoo, and it contains an anionic, nonionic or amphoteric surfactant. Anionic surfactants are preferred, such as the alkali, ammonium or alkanolamine salts of alkane sulfonates, alkyl sulfonates, and alkyl ether sulfates, in which the alkyl radical has from 12 to 18 carbon atoms. Lauryl or tetradecyl ether sulfates, the disodium salt of the sulfosuccinic semiester of alkanolamides, and polyether carboxylic acids are especially preferred.

Among the nonionic surfactants, the ethoxylated fatty alcohols with from 12 to 18 carbon atoms, such as ethoxylated lauryl, tetradecyl, cetyl, oleyl and stearyl alcohol with up to 40 Mol ethylene oxide per fatty alcohol, can be named and can be used either alone or in mixture. Ethoxylated lanolin and the fatty alcohols of ethoxylated lanolin are also highly suitable. Polyglyceryl ethers of saturated or unsaturated fatty alcohols and alkyl phenols with from 8 to 30 carbon atoms in the alkyl radical and 1 to 10 glyceryl units in the molecule can also be employed. Fatty acid alkanolamides as well as ethoxylated sorbitan fatty acid esters can also be employed in the hair cleaning preparation of the invention.

As amphoteric or amphionic surfactants, above all the N-alkylbetaines, N-alkylaminobetaines, N-alkylsulfobetaines, N-alkylaminopropionates, dialkyldimethylammonium acetates, and the fatty acid alkylamidobetaines can be named.

The hair cleaning preparation of the invention includes the aforementioned surfactants either singly or in mixture in aqueous solution. To improve the shine, a mixture of fruit acids and pantothenol or one of its derivatives is added. Citric acid, lactic acid, maleic acid, tartaric acid, gluconic acid, or dicarboxylic acids such as fumaric acid or succinic acid can be named as the fruit acids. It is a requirement that the quantity of fruit acids employed be at least 2 weight percent, referred to the total quantity of hair cleaning preparation. With lesser quantities of fruit acids, no improvement to the shine can be ascertained visually. To prevent the occurrence of an overly acidic pH value from the use of large quantities of fruit acids, it is necessary to adjust the pH value of the skin cleaning agent of the invention by adding alkali until the pH value is in the range between 4 and 7 and preferably between 4.5 and 5.6.

The use of a mixture of citric acid and lactic acid is preferred, which should be mixed together in a ratio of from 1:9 to 9:1 but preferably in approximately equal quantities.

As a further ingredient in the hair cleaning preparation of the invention, pantothenol or one of its derivatives, in particular pantothenic acid and its esters, are responsible for the shine-lending effect of the hair cleaning preparation of the invention.

Its is understood that in addition to the above ingredients, other typical cosmetic additives can be added to the hair cleaning preparation, such as perfume oils, pearlescent agents, completing agents, dyes, preservatives, pH buffer substances, or polysiloxanes as conditioning agents.

The hair cleaning preparation of the invention may also contain dyes for direct dying of hair, in which they can be used as so-called "tinting or dyeing shampoo".

Further typical cosmetic additives for hair cleaning preparations are described in "Die kosmetischen Präparate" [Cosmetic Preparations] by Andreas Domsch, 4th Edition, Vol. 2, pp. 212–230.

To visually improve the shine of hair washed with the hair cleaning preparation of the invention and dried, the formations described in Table 1 below were compared with one another. All the quantities indicated are given as percentages and refer to the total quantity of hair cleaning preparation of the invention.

TABLE 1

COMPARISON OF HAIR CLEANING COMPOSITION A OF THE INVENTION WITH VARIOUS PRIOR ART COMPOSITIONS

|  | A | B | C | D |
|---|---|---|---|---|
| Sodium laurethsulfate | 9.80 | 9.80 | 9.80 | 9.80 |
| Cocamidopropylbetaine | 1.50 | 1.50 | 1.50 | 1.50 |
| Pantothenol | 0.30 | 0.30 | — | — |
| Citric acid | 1.00 | — | 2.00 | — |
| Lactic acid | 1.00 | — | — | 2.00 |

TABLE 1-continued

COMPARISON OF HAIR CLEANING COMPOSITION A OF THE INVENTION WITH VARIOUS PRIOR ART COMPOSITIONS

|  | A | B | C | D |
|---|---|---|---|---|
| Perfume | 0.40 | 0.40 | 0.40 | 0.40 |
| Sodium chloride | 1.00 | 1.00 | 1.00 | 1.00 |
| Preservative | 0.50 | 0.50 | 0.50 | 0.50 |
| Water | To make up 100 | To make up 100 | To make up 100 | To make up 100 |
| Professional result compared with A: | Standard | Negative | Negative | Negative |

The professional assessment of the shine of hair washed with the agents A, B, C and D and dried is that a superior shine effect was achieved with agent A according to the invention, while agents B, C and D did not produce any visually perceptible increase to the shine of the dried hair.

The examples below explain the composition of the hair cleaning preparation of the invention in still more detail:

EXAMPLE 1

Clear Shine-Promoting Shampoo

A preparation, made from inexpensive starting ingredients, of the hair cleaning preparation (A) of the invention was compared with a convention hair cleaning preparation (B).

|  | A | B |
|---|---|---|
| Sodium laurethsulfate | 40.00 | 40.00 |
| Lactic acid | 1.00 | — |
| Citric acid | 1.00 | — |
| Pantothenol | 0.30 | — |
| Perfume | 0.30 | 0.30 |
| Sodium chloride | 2.80 | 2.80 |
| Preservative | 0.50 | 0.50 |
| Water | To make up 100 | To make up 100 |

All the quantities are given in the form of percentages and refer to the total quantity of hair cleaning preparation. The shampoo in formulation A, compared with shampoo B, produces considerably more shine on dried hair.

EXAMPLE 2

Pearlescent Shine-Promoting Shampoo

|  | A | B |
|---|---|---|
| Sodium laurethsulfate | 35.00 | 35.00 |
| Cocamidopropylbetaine | 5.00 | 5.00 |
| PEG-S distearate | 2.00 | 2.00 |
| Polyquaternium-10 | 0.10 | 0.10 |
| Lactic acid | 1.00 | — |
| Citric acid | 1.00 | — |
| Pantothenol | 0.30 | — |
| Perfume | 0.50 | 0.50 |
| Sodium chloride | 2.80 | 2.80 |
| Preservative | 0.50 | 0.50 |
| Water | To make up 100 | To make up 100 |

Shampoo A produces considerably more shine on dried hair than shampoo B.

What is claimed is:

1. A hair cleaning preparation in the form of an aqueous solution or emulsion with shine-enhancing properties, said hair cleansing preparation consisting of:

water;

from 5 to 50 percent by weight of at least one surfactant selected from the group consisting of anionic, nonionic and amphoteric surfactant compounds;

from 2 to 10 percent by weight of a mixture of at least two fruit acids selected from the group consisting of lactic acid, citric acid, maleic acid, tartaric acid, gluconic acid, fumaric acid and succinic acid;

from 0.2 to 2 percent by weight of at least one ingredient selected from the group consisting of pantothenol, pantothenic acid and esters of pantothenic acid; and at least one cosmetic ingredient selected from the group consisting of perfume oils, preservatives, sodium chloride and pH buffer substances;

with the proviso that the hair cleaning preparation does not contain any oily or greasy ingredients.

2. The hair cleaning preparation as defined in claim 1, having a pH of from 4 to 7.

3. The hair cleaning preparation as defined in claim 2, wherein said pH is from 4.5 to 5.6.

4. The hair cleaning preparation as defined in claim 1, wherein said mixture consists of said citric acid and said lactic acid mixed together in a ratio of from 1:9 to 9:1.

5. The hair cleaning preparation as defined in claim 1, wherein said mixture consists of said citric acid and said lactic acid mixed together in approximately equal amounts.

6. A method of increasing shine on hair, said method comprising the steps of:

a) providing a hair cleaning preparation in the form of an aqueous solution or emulsion with shine-enhancing properties, said hair cleansing preparation consisting of water; from 5 to 50 percent by weight of at least one surfactant selected from the group consisting of anionic, nonionic and amphoteric surfactant compounds; from 2 to 10 percent by weight of a mixture of at least two fruit acids selected from the group consisting of lactic acid, citric acid, maleic acid, tartaric acid, gluconic acid, fumaric acid and succinic acid; from 0.2 to 2 percent by weight of at least one ingredient selected from the group consisting of pantothenol, pantothenic acid and esters of pantothenic acid; and at least one cosmetic ingredient selected from the group consisting of perfume oils, preservatives, sodium chloride and pH buffer substances, with the proviso that the hair cleaning preparation does not contain any oily or greasy ingredients;

b) washing the hair with the hair cleaning preparation provided in step a); and c) after the washing of step b), drying the hair.

* * * * *